US009812002B2

(12) United States Patent
He et al.

(10) Patent No.: US 9,812,002 B2
(45) Date of Patent: Nov. 7, 2017

(54) WIRELESS COMMUNICATION AUTHENTICATION FOR MEDICAL MONITORING DEVICE

(71) Applicant: ABBOTT DIABETES CARE INC., Alameda, CA (US)

(72) Inventors: Lei He, Moraga, CA (US); Marc B. Taub, Mountain View, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 15/133,991

(22) Filed: Apr. 20, 2016

(65) Prior Publication Data
US 2017/0018172 A1   Jan. 19, 2017

Related U.S. Application Data

(63) Continuation of application No. 13/722,223, filed on Dec. 20, 2012, now Pat. No. 9,344,777.

(51) Int. Cl.
*G08C 17/02* (2006.01)
*H04Q 9/00* (2006.01)
(Continued)

(52) U.S. Cl.
CPC ............ *G08C 17/02* (2013.01); *A61B 5/0004* (2013.01); *A61B 5/0015* (2013.01);
(Continued)

(58) Field of Classification Search
CPC ................ G08B 21/02; G08B 21/0453; G08B 21/0446; G08B 25/016; A61B 5/14532;
(Continued)

(56) References Cited

U.S. PATENT DOCUMENTS

| 5,507,288 A | 4/1996 | Bocker et al. |
| 2006/0226990 A1 | 10/2006 | Broad et al. |

(Continued)

FOREIGN PATENT DOCUMENTS

EP   0880936 A2   12/1988

OTHER PUBLICATIONS

WO, PCT/US2013/071790 ISR and Written Opinion, dated Mar. 20, 2014.
EP, 13865710.1 Supplementary Search Report, dated Nov. 16, 2016.

*Primary Examiner* — Kerri McNally
*Assistant Examiner* — Sharmin Akhter
(74) *Attorney, Agent, or Firm* — One LLP (57) ABSTRACT

Methods, systems, and devices for short-range low-power wireless communication of analyte information are provided. In some implementations, short-range low-power wireless communication of analyte information may include receiving an electromagnetic wireless communication signal and harvesting energy from the electromagnetic wireless communication signal. In some implementations, short-range low-power wireless communication of analyte information may include enabling capabilities associated with an external sensor in response to detecting the external sensor. In some implementations, short-range low-power wireless communication of analyte information may include detecting an analyte sample; determining an analyte concentration associated with the detected analyte sample; and transmitting an indication of the analyte concentration to an external device.

18 Claims, 6 Drawing Sheets

(51) Int. Cl.
*A61B 5/00* (2006.01)
*A61B 5/145* (2006.01)
*H02J 3/38* (2006.01)
*H04B 5/00* (2006.01)
*H04W 4/00* (2009.01)

(52) U.S. Cl.
CPC .......... *A61B 5/14532* (2013.01); *H02J 3/383* (2013.01); *H02J 3/387* (2013.01); *H04B 5/0031* (2013.01); *H04Q 9/00* (2013.01); *H04W 4/008* (2013.01); *A61B 5/14546* (2013.01); *A61B 2560/0214* (2013.01); *H04Q 2209/43* (2013.01); *H04Q 2209/47* (2013.01); *H04Q 2209/886* (2013.01); *Y02B 60/50* (2013.01)

(58) Field of Classification Search
CPC .............. A61B 5/14552; A61B 5/0205; A61B 5/1455; A61B 5/14546; A61B 5/14551
USPC ............... 600/316–347, 365; 340/10.1–10.6, 340/539.12, 870.02
See application file for complete search history.

(56) References Cited

U.S. PATENT DOCUMENTS

| | | |
|---|---|---|
| 2008/0191876 A1 | 8/2008 | Kostrzewski et al. |
| 2009/0171178 A1 | 7/2009 | He et al. |
| 2009/0216100 A1* | 8/2009 | Ebner et al. .................. 600/347 |
| 2009/0221897 A1 | 9/2009 | Nieuwkoop |
| 2010/0076615 A1 | 3/2010 | Daniel et al. |
| 2010/0198032 A1* | 8/2010 | Simpson ............. A61B 5/0002 600/365 |
| 2011/0144463 A1 | 6/2011 | Pesach et al. |
| 2011/0149759 A1 | 6/2011 | Jollota |
| 2012/0013296 A1* | 1/2012 | Heydari et al. ............... 320/108 |
| 2012/0255875 A1 | 10/2012 | Vicente et al. |
| 2012/0259188 A1 | 10/2012 | Besling |
| 2012/0307538 A1 | 12/2012 | Ramorini et al. |
| 2012/0316414 A1* | 12/2012 | Greene ......................... 600/365 |
| 2014/0073892 A1* | 3/2014 | Randloev ............ G06F 19/3437 600/365 |
| 2014/0107444 A1* | 4/2014 | Liu ............................... 600/345 |

\* cited by examiner

WIRELESS COMMUNICATION AUTHENTICATION FOR MEDICAL MONITORING DEVICE

CROSS-REFERENCE TO RELATED APPLICATION

The present application is a continuation of U.S. patent application Ser. No. 13/722,223, filed Dec. 20, 2012, which is incorporated herein by reference in its entirety for all purposes.

TECHNICAL FIELD

The embodiments herein relate in general to a device and method for determining and reporting glucose readings using wireless communication.

BACKGROUND

Analyte monitoring systems, such as glucose monitoring systems, including continuous and discrete monitoring systems, may include a battery powered and microprocessor controlled system which is configured to detect signals proportional to the corresponding measured glucose levels using an electrometer, and transmit the collected data, such as via radio frequency (RF) transmission. In some implementations, glucose monitoring systems may include a transcutaneous or subcutaneous analyte sensor configuration which may be, for example, partially mounted on the skin of a subject whose glucose level is to be monitored. The sensor may use a two or three electrode (work, reference, and counter electrodes) configuration driven by a controlled potential (potentiostat) analog circuit connected through a contact system.

In view of the foregoing, it would be desirable to provide a short-range low-energy communication unit in a data monitoring and management system.

BRIEF SUMMARY

In accordance with the various embodiments of the present disclosure, there are provided methods, devices, and systems for providing a short-range low-energy communication unit in a data monitoring and management system.

In a first aspect, the present disclosure provides a device, including a housing, a processor coupled to the housing, a memory unit configured to store computer executable instructions, an antenna, an energy scavenging unit, and a processor configured to execute the computer executable instructions stored in the memory to control the energy scavenging unit to harvest energy from an electromagnetic signal received by the antenna, detect an analyte sample, determine an analyte concentration associated with the detected analyte sample, and transmit an indication of the analyte concentration to an external device using the harvested energy.

In a second aspect, the present disclosure provides a method including receiving an electromagnetic wireless communication signal, harvesting energy from the electromagnetic wireless communication signal, detecting an analyte sample, determining an analyte concentration associated with the detected analyte sample, and transmitting an indication of the analyte concentration to an external device using the harvested energy.

In a third aspect, the present disclosure provides a device, including a housing, a memory unit configured to store computer executable instructions, a transceiver, a plurality of capabilities associated with an external sensor, wherein each capability in the plurality of capabilities associated with the external sensor is disabled, and a processor configured to execute the computer executable instructions stored in the memory to enable an external sensor interface, search for the external sensor, in response to detecting the external sensor, enable each capability in the plurality of capabilities associated with the external sensor, detect an analyte sample using the external sensor interface, determine an analyte concentration associated with the detected analyte sample, and transmit an indication of the analyte concentration to an external device.

In a fourth aspect, the present disclosure provides a method including enabling an external sensor interface, wherein the external sensor interface is one of a plurality of capabilities associated with an external sensor, wherein each capability in the plurality of capabilities associated with the external sensor is disabled, searching for the external sensor, in response to detecting the external sensor, enabling each capability in the plurality of capabilities associated with the external sensor, detecting an analyte sample using the external sensor interface, determining an analyte concentration associated with the detected analyte sample, and transmitting an indication of the analyte concentration to an external device.

It should be noted that two or more of the embodiments described herein, including those described above, may be combined to produce one or more additional embodiments which include the combined features of the individual embodiments.

These and other objects, features, and advantages of the present disclosure will become more fully apparent from the following detailed description of the embodiments, the appended claims and the accompanying drawings.

DETAILED DESCRIPTION

As described in accordance with the various embodiments of the present disclosure below, there are provided methods and systems for utilizing short-range low-energy wireless communications in an electronic device used in analyte monitoring and management systems, such as in a glucose monitoring and management systems.

Although FIGS. 1-8 are described with reference to glucose monitoring, any data monitoring and management system may be used. For example, an analyte monitoring system may monitor a variety of analytes, such as, lactate, ketones, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. In some implementations, the concentration of drugs, such as, for example, antibiotics (e.g., gentamicin, vancomycin, and the like), digitoxin, digoxin, drugs of abuse, theophylline, and warfarin, may be monitored.

Figure 1:
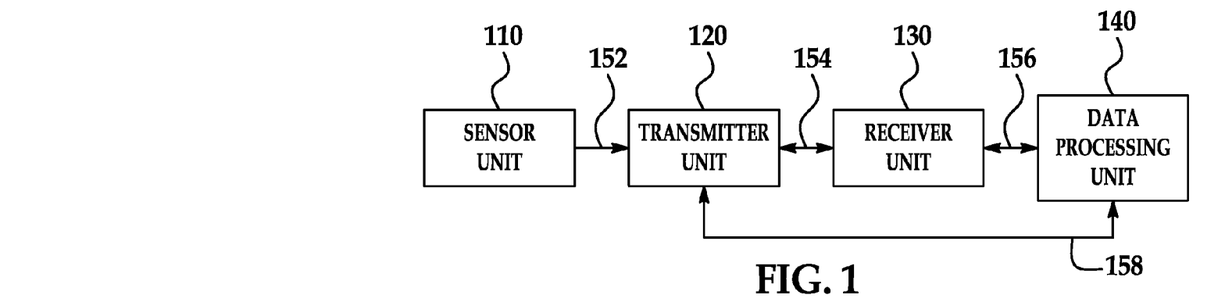
FIG. 1 shows a block diagram of an analyte data monitoring and management system in accordance with embodiments of the present disclosure.

FIG. 1 shows a block diagram of an analyte data monitoring and management system 100, such as a glucose monitoring system, in accordance with embodiments of the present disclosure. The analyte data monitoring and management system 100 may include a sensor unit 110, a transmitter unit 120, a receiver unit 130, a data processing unit 140, or any combination thereof.

In some implementations, one or more of the sensor unit 110, the transmitter unit 120, the receiver unit 130, or the data processing unit 140 may be configured to communicate via a wired or wireless communication link 152/154/156/158. For example, communicating via a wireless communication link may include using one or more of a radio frequency (RF) communication protocol, a near field communication (NFC) protocol, a radio frequency identification (RFID) protocol, an infrared communication protocol, a Bluetooth® communication protocol, an 802.11x wireless communication protocol, or an equivalent wireless communication protocol which may provide secure, wireless communication with one or more units while avoiding data collision and interference.

The sensor unit 110 may communicate with the transmitter unit 120 to provide monitored or detected analyte information. The sensor unit 110 may communicate the analyte information in response to manual interaction, based on a transmission schedule, or in response to a request from the transmitter unit 120.

In some implementations, the sensor unit 110 may be a test strip, which may be an electrochemical analyte test strip, such as a blood glucose test strip or other fluid sample reception unit. The test strip may be mechanically received in a test strip port of the transmitter unit 120, which may be a hand-held blood glucose meter.

In some implementations, the sensor unit 110 may be an external monitoring device, such as a continuous analyte monitoring device. For example, the sensor unit 110 may be physically positioned in or on the body of a user whose glucose level is being monitored, and the sensor unit 110 may continually or substantially continually measure an analyte concentration of a bodily fluid. In some embodiments, the sensor unit 120 may be configured as a compact, low profile on-body patch device assembled in a single integrated housing and positioned on a skin surface of the user or the patient with a portion of the analyte sensor maintained in fluid contact with a bodily fluid such as an interstitial fluid. The sensor unit 110 may be configured to continuously sample the glucose level of the user and convert the sampled glucose level into a corresponding data signal for transmission by the transmitter unit 120.

The transmitter unit 120 may be configured to receive analyte information from the sensor unit 110. For example, the transmitter unit 120 may be configured to receive a fluid sample transported by a test strip. In another example, the transmitter unit 120 may be configured to receive analyte data from an external monitoring device, such as a continuous analyte monitoring device. In another example, the transmitter unit 120 may be configured to receive a fluid sample transported by a test strip and to receive analyte data from an external monitoring device. In some embodiments, the transmitter unit 120 may be configured to control the sensor unit 110.

The transmitter unit 120 may be configured to communicate with the receiver unit 130 via a communication link 154. In some embodiments, the transmitter device 120 may be configured without a user interface or display to minimize the size and cost of the transmitter device 120. In some embodiments, the transmitter unit 120 may be mounted on the sensor unit 110, or the sensor unit 110 and the transmitter unit 120 may be configured as a combined unit, and both units may be positioned on a user's body. The transmitter unit 120 may perform data processing such as filtering and encoding of data signals, each of which may correspond to a sampled glucose level of the user, for transmission to the receiver unit 130 via the communication link 154.

In some embodiments, the communication link 154 may be unidirectional from the transmitter unit 120 to the receiver unit 130. The transmitter unit 120 may transmit sampled data signals received from the sensor unit 110 without acknowledgement from the receiver unit 130. For example, the transmitter unit 120 may be configured to transmit encoded sampled data signals at a fixed rate (e.g., at one minute intervals) after the completion of an initial power on procedure. The receiver unit 130 may be configured to detect transmitted encoded sampled data signals at predetermined time intervals.

The receiver unit 130 may be configured to receive data from the transmitter unit 120 via communication link 154 and to transmit data to the data processing unit 140 for evaluation via communication link 156. In some implementations, the receiver unit 130 may include an analog interface unit, which may be configured to communicate with the transmitter unit 120 via the communication link 154, and a data processing unit, which may be configured to process data signals received from the transmitter unit 120, by performing, for example, data decoding, error detection and correction, data clock generation, or data bit recovery. In some embodiments, the analog interface section may include or wireless communication receiver and an antenna for receiving and amplifying the data signals from the transmitter unit 120. The signals may be processed at the receiver unit 130. For example, the signals may be demodulated with a local oscillator and filtered through a band-pass filter.

In some implementations, the receiver unit 130 may be configured to detect the presence of the transmitter unit 120 within a range based on, for example, the strength of the detected data signals received from the transmitter unit 120 or based on predetermined transmitter identification information. The receiver unit 130 and the transmitter unit 120 may synchronize and the receiver unit 130 may receive data signals corresponding to the user's detected glucose level from the transmitter unit 120. For example, the receiver unit 130 may be configured to perform synchronized time hopping with the corresponding synchronized transmitter unit 120 via the communication link 154 to obtain the user's detected glucose level.

In some embodiments, the receiver unit 130 may include a PDA or smartphone, which may synchronize data with the data processing unit 140, which may be a personal computer (PC). In another embodiment, the receiver unit 130 may include a mobile phone, which may communicate via a cellular network with the data processing unit 140, which may be a computer system at, for example, a physician's office.

The data processing unit 140 may be configured to evaluate data received from the receiver unit 130. In some implementations, the data processing unit 140 may be configured to communicate directly with the transmitter unit 120 via communication link 158. In some implementations, the receiver unit 130 may be configured to include the functions of the data processing unit 140 such that the receiver unit 130 may be configured to receive and evaluate data from the transmitter unit 120.

In some implementations, the data processing unit 140 may include a personal computer, a portable computer such as a laptop or a handheld device (e.g., a personal digital assistant (PDA) or smartphone), and the like, and may be configured for data communication with the receiver unit 130 via a wired or a wireless communication link. In some embodiments, the data processing unit 140 may be connected to a data network (not shown) for storing, retrieving and updating data corresponding to the detected glucose level of the user.

In some implementations, the data processing unit 140 may include an infusion device such as an insulin infusion pump or the like, which may be configured to administer insulin to patients, and which may be configured to communicate with the receiver unit 130 for receiving, for example, glucose level measurements. In some embodiments, the receiver unit 130 may be integrated with an infusion device and the receiver unit 130 may be configured to administer insulin therapy to patients, for example, for administering and modifying basal profiles, as well as for determining appropriate boluses for administration based on, for example, the detected glucose levels received from the transmitter unit 120.

In some implementations, the data processing unit 140 may be configured to receive signals including glucose information from the transmitter unit 120, and may incorporate functions of the receiver unit 130, which may include data processing for managing the patient's insulin therapy and glucose monitoring.

Although FIG. 1 shows a sensor unit 110, a transmitter unit 120, a receiver unit 130, and a data processing unit 140, the glucose monitoring communication system 100 may include multiple sensors, multiple transmitters, multiple communication links, multiple receivers, or multiple data processing units. In some implementations, the glucose monitoring communication system 100 may be a continuous monitoring system, a semi-continuous monitoring system, or a discrete monitoring system. For example, the sensor unit 110 may be configured as a test strip, the transmitter unit 120 may be configured as a hand-held blood glucose monitor, and the receiver unit 130 and the data processing unit 140 may be omitted. In another example, the sensor unit 110 may be configured as an external monitoring device, the transmitter unit 120 may be configured as small device without a user interface to receive information from and control the sensor unit 110, and the receiver unit 130 may be configured to receive information from and control the transmitter unit 120 and to provide a user interface for the system.

Figure 2:
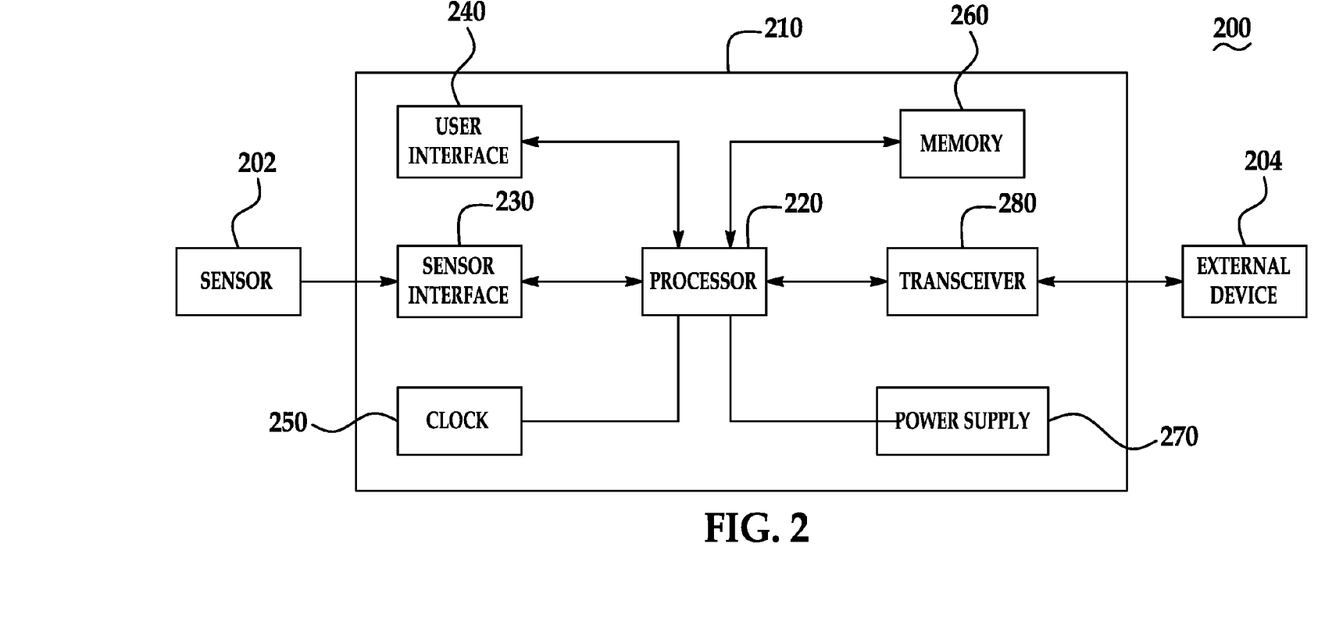
FIG. 2 shows a diagram of a health monitor device in accordance with embodiments of this disclosure.

FIG. 2 shows a diagram of a health monitor device 200 in accordance with embodiments of this disclosure. The health monitor device 200 may include a client device, such as the transmitter unit 120 shown in FIG. 1, a server device, such as the receiver unit 130 shown in FIG. 1, or both. The health monitor device 200 may be used for determining a concentration of an analyte in blood or interstitial fluid. For example, the health monitor device 200 may be an analyte test meter, such as a glucose test meter that may be used for determining an analyte concentration, such as a blood glucose concentration, of a sample for determination of a blood glucose level of a patient, such as a patient with Type-1 or Type-2 diabetes. In some embodiments, the health monitor device 200 may be a blood glucose meter, a continuous monitor, an insulin pump, a blood pressure meter, a heart rate monitor, a thermometer, or any other health monitor device capable of measuring, monitoring, or storing raw or analyzed medical data electronically.

The health monitor device 200 may communicate in a wireless communication system, such as the system shown in FIG. 1. For example, the health monitor device 200 may receive fluid samples, or sample data, from a sensor device 202, such as the sensor unit 110 shown in FIG. 1, and may wirelessly transmit data to an external device 204, such as the receiver unit 130 or the data processing unit 140 shown in FIG. 1. The health monitor device 200 may include a housing 210, a processor 220, a sensor interface 230, a user interface 240, a clock 250, a data storage unit 260, a power supply 270, a communication interface 280, or a combination thereof.

The housing 210 may physically enclose one or more of the processor 220, the sensor interface 230, the user interface 240, the clock 250, the data storage unit 260, the power supply 270, or the communication interface 280, and may be configured to fit into a small profile. Although the housing 210 is shown a single physical unit, the housing 210 may be implemented as one or more physical units that may be physically or electronically connected. Although not shown in FIG. 2, the housing 210 may include one or more ports, such as a test strip port, a power port, an audio connection port, or a data connection port. For example, the housing 210 may include a test strip port configured to receive a test strip, which may include a fluid sample, and may be connected to the sensor interface 230.

The processor 220 may include any device capable of manipulating or processing a signal or other information, including an optical processor, a quantum processor, a molecular processor, or a combination thereof. For example, the processor 220 may include a general purpose processor, a central processing unit (CPU), a special purpose processor, a plurality of microprocessors, a controller, a microcontroller, an Application Specific Integrated Circuit (ASIC), a Field Programmable Gate Array (FPGA), a programmable logic array, programmable logic controller, microcode, firmware, any type of integrated circuit (IC), a state machine, or any combination thereof. As used herein, the term "processor" includes a single processor or multiple processors. The processor 220 may be operatively coupled to the sensor interface 230, the user interface 240, the clock 250, the data storage unit 260, the power supply 270, or the communication interface 280.

In some embodiments, the sensor interface 230 may receive a fluid sample. For example, the sensor 202 may be a test strip and the sensor interface 230 may receive a fluid sample transported via a test strip. The processor 220 may control the sensor interface 230 to analyze the fluid sample to determine an associated analyte level.

In some embodiments, the sensor interface 230 may receive raw or analyzed data indicating an analyte level associated with a fluid sample analyzed at an external measurement device, such as a continuous analyte monitoring device, via a wireless communication medium, such as radio frequency identification (RFID). For example, the continuous analyte monitoring device may include a transcutaneously implanted sensor, such as an implantable glucose sensor, that may continually or substantially continually measure an analyte concentration of a bodily fluid. In some embodiments, the sensor interface 230 may receive analyte related data from the external measurement device periodically, based on a transmission schedule, or may request the data from the external measurement device.

The user interface 240 may include a display unit and one or more input elements, which may include physical input elements, such as buttons, jogs, or dials, virtual input elements, such as butts on a touch screen, or both. The user interface 240, or a portion thereof, may be integrated with the housing 210. For example, the user interface 240 may form a part of an external surface of the housing 210. The user interface 240, or a portion thereof, may be configured to allow a user of the health monitor device 200 to receive information, input information, or otherwise interact, with the health monitor device 200. For example, the user of the health monitor device 200 may operate the one or more input buttons to enter a calibration code associated with a test strip or other fluid sample reception device. In another example, the user interface 240 may present visual, tactile, or auditory information indicating, for example, a blood glucose measurement to the user. In some embodiments, the display unit may include a graphical display unit, such as a LCD or an LED display, an auditory display unit, such as speaker, or both a graphical display and an audio display. In some embodiments, the user interface 240 may include a touch screen display. In some embodiments, the display unit, the input elements, or both may be omitted from the user interface 240.

The clock 250 may be operatively coupled to the processor 220 and may provide a clock signal at discreet clock frequencies to the processor 220. For example, the clock may include an oscillator, such as a quartz crystal oscillator, or any other device capable of producing a clock signal for indicating a real time clock.

The data storage unit 260 may store raw data, analyzed data, or both. In some embodiments, the data storage unit 260 may store instructions that may be executed by the processor to, for example, perform analysis, such as analyte concentration analysis and medication dosage calculation. The data storage unit 260 may include any non-transitory computer-usable or computer-readable medium, such as any tangible device that can, for example, contain, store, communicate, or transport instructions, or any information associated therewith, for use by or in connection with the processor 220. The non-transitory computer-usable or computer-readable medium may be, for example, a solid state drive, a memory card, removable media, a read only memory (ROM), a random access memory (RAM), any type of disk including a hard disk, a floppy disk, an optical disk, a magnetic or optical card, an application specific integrated circuits (ASICs), or any type of non-transitory media suitable for storing electronic information, or any combination thereof. The data storage unit 260 may be operatively connected to, for example, the processor 220 through, for example, a memory bus.

The power supply 270 may be any suitable device for powering the health monitor device 200, or any portion thereof. For example, the power supply 270 may include a wired power source; one or more dry cell batteries, such as nickel-cadmium (NiCd), nickel-zinc (NiZn), nickel metal hydride (NiMH), lithium-ion (Li-ion); solar cells; fuel cells; or any other device capable of powering the health monitor device 200. The processor 220, the sensor interface 230, the user interface 240, the clock 250, the data storage unit 260, or the communication interface 280, may be operatively coupled to the power supply 270.

The communication interface 280 may communicate with an external device 204, such as the receiver unit 130 shown in FIG. 1. For example, the communication interface 280 may be an RF transmitter and may communicate using a wireless communication protocol, such as an 802.11 protocol, a Bluetooth® protocol, a cellular protocol, or any other wireless protocol. In some embodiments, the communication interface 280 may include a receiver, a transmitter, or a transceiver. For example, the communication interface 280 may include a wireless transmission unit, such as a Bluetooth® low-energy wireless transmission unit. Although not expressly shown in FIG. 2, the communication interface 280 may include a wireless antenna, a wired communication port, such as an Ethernet port, an infrared port, a serial port, or any other wired or wireless unit capable of interfacing with a wired or wireless electronic communication medium. In some embodiments, the health monitor device 200 may communicate with the external device 204 indirectly via another device, or series of devices. For example, the health monitor device 200 may communicate with the external device 204 via a network, wherein the health monitor device 200 may transmit signals to, for example, an access point (not shown), and the access point may transmit the signals to the external device 204, in the same or a different format, via one or more other devices in a network.

In some embodiments, the health monitor device 200 may audibly present information, such as information indicating an analyte concentration, information indicating a rate of change of an analyte concentration, or information indicating the exceeding of a threshold of an analyte concentration, which may indicate, for example, hypo- or hyperglycemia. For example, the user interface 240 may include a speaker, and the health monitor device 200 may present the audio signal via the speaker. In some embodiments, the health monitor device 200 may transmit raw or analyzed analyte information to the external device 204 and the external device 204 may generate an audio signal for presentation. In some embodiments, the health monitor device 200 may generate an audio signal indicating the information and may transmit the audio indication to the external device 204 for audio presentation.

Although shown as separate elements, the processor 220, the sensor interface 230, the user interface 240, the clock 250, the data storage unit 260, the power supply 270, the communication interface 280, or any combination thereof, may be integrated in one or more electronic units, circuits, or chips.

Figure 3:
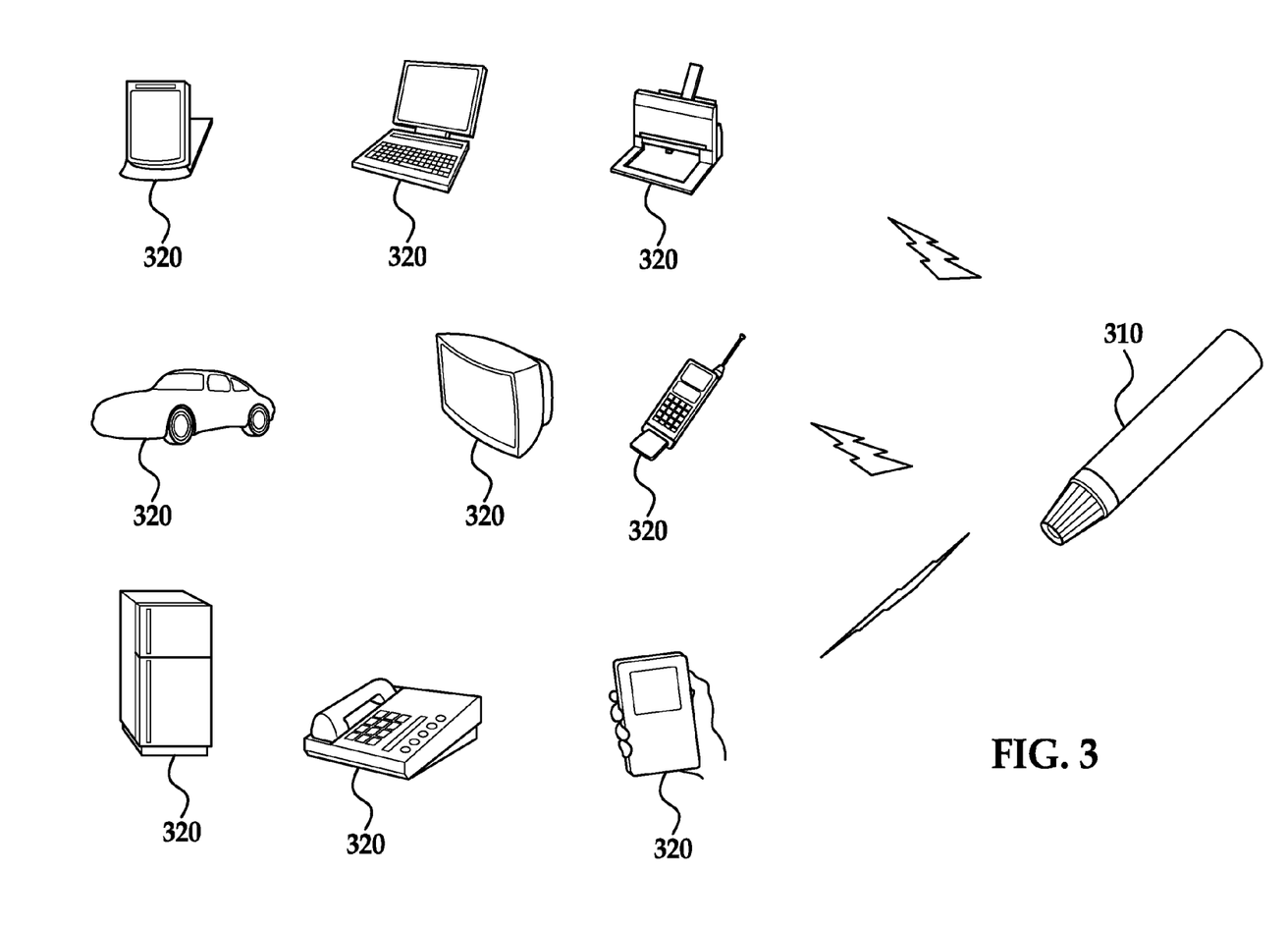
FIG. 3 shows examples of a health monitor device in communication with external devices in accordance with embodiments of this disclosure.

FIG. 3 shows examples of a health monitor device 310, such as the health monitor device 200 shown in FIG. 2, in communication with external devices 320, such as the receiver device 130 or the data processing unit 140 shown in FIG. 1 in accordance with embodiments of this disclosure. The health monitor device 310 and one or more of the external devices 320 may be part of a communication network, such as an individual's personal area network, and may be capable of wireless communication.

In some embodiments, the external device 320 may be a desktop computer, laptop computer, a handheld computer, or a printer, and may be configured to provide displays and printouts of detected or monitored information. In some embodiments, the external device 320 may be a telephone that may be configured to display glucose data as and to transmit the data over a larger network.

In some embodiments, the external device 320 may be a configured to assist an individual by responding to glucose levels by providing alarms, suggesting that action be taken to correct a hypo or hyperglycemic condition, or to call necessary medical assistance. For example, individuals may be aware of the risks involved in driving when glucose levels are out of range and particularly when they are too low. Thus, a navigation computer, or other electronic device, in an individual's car may become part of the local area network and may download glucose data from the meter. For safety, the car computer system may be programmed to require that the individual to perform a glucose test before driving, and the car may be disabled unless the diabetic takes the test and the result is in an appropriate range.

Figure 4:
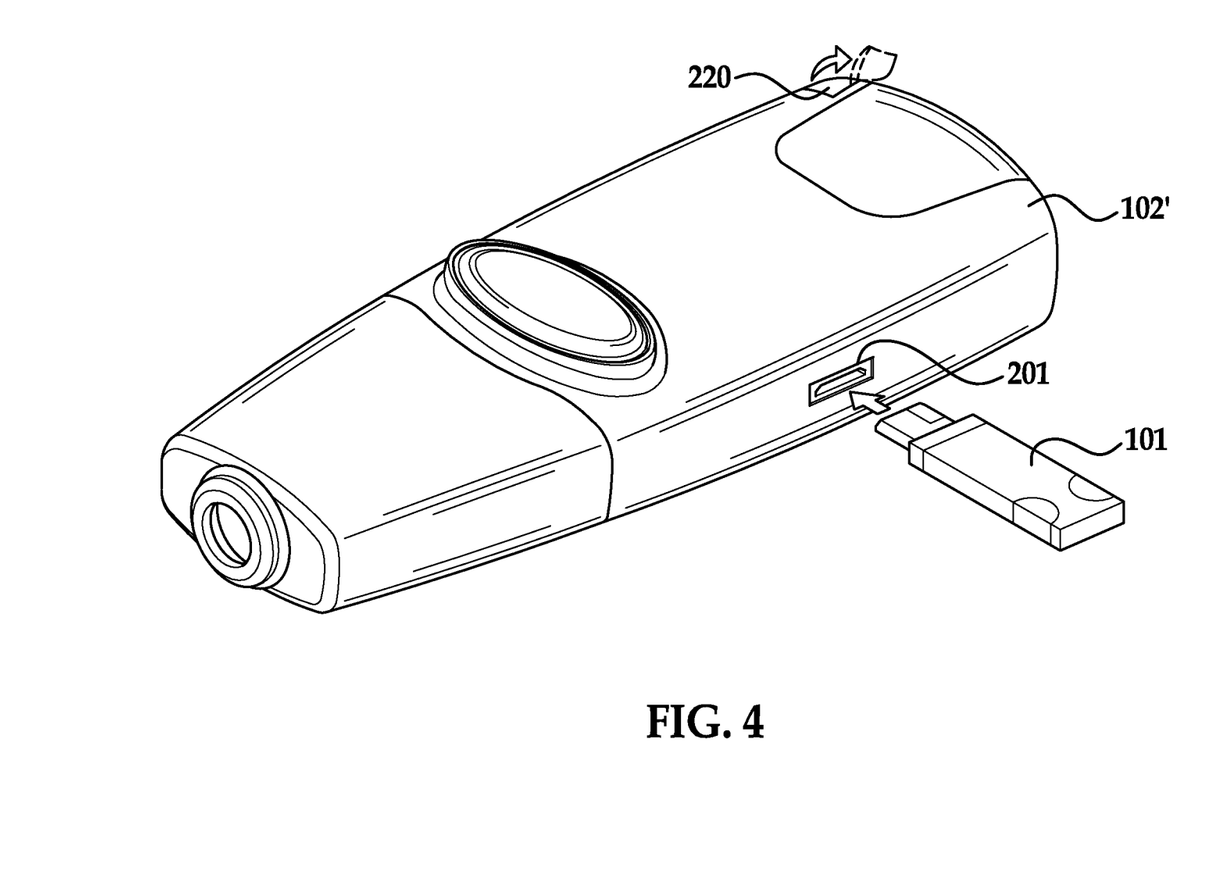
FIG. 4 shows a perspective view diagram of a health monitor device in accordance with embodiments of this disclosure.

FIG. 4 shows a schematic of a health monitor device in accordance with embodiments of this disclosure. In some implementations, a blood glucose meter 102 may not include a display or push buttons and may be combined with a lancing device to form an integrated unit 102'. Test strip port 201 can be located in the side of integrated device 102' or in any other appropriate position. A test strip storage compartment can be located within integrated device 102' and accessed through a flip-lid 220 or other suitable closure means. A second test strip storage compartment (not shown) can be included so that fresh strips and used strips can be separately stored. A desiccant may be provided in one of the storage compartments to preserve the fresh strips. By integrating these features together in a single device without a user interface, the typical test kit that is carried around by people with diabetes can be made much smaller, easier to handle, and less costly.

A user may use a larger display unit within his or her personal area network, which can be synchronized as they interact and communicate with the wireless enabled meter. The sequences through which the user must "step" to complete tests (e.g. entering the calibration code, prompting application of the sample) may be readily viewed on the larger display units. The meter unit may be simplified, and may be smaller and less expensive to manufacture. Control buttons may be eliminated, saving additional size and cost, since the user can use interface features of the external device. Simplified, wireless enabled meters may be disposable, for example, after a specified number of uses, permitting the producer to routinely upgrade as appropriate.

The system may permit the user to include security coding at any time the meter unit accesses a display device, so that the user's data is secure. For example, when the health monitor device is used, that the system may request the user enter an identity code in order to verify that the person handling the meter is an authorized user. The system to permit more than one user. The user data may be encrypted prior to wireless transmission and thereafter respectively decrypted upon wireless reception.

In some implementations, the health monitor device may be configured to advise the user of a glucose level which is determined when the module is used as a "stand-alone" unit. For example, the module may include a very low cost, small three digit LCD display. In another example, the module may include LED indicator lights, a column of LEDs, or an electroluminescent strip to indicate approximate or relative glucose levels. For example, the health monitor device may include a red LED for below range, a green LED for within range, and a yellow LED for above range.

Figure 5:
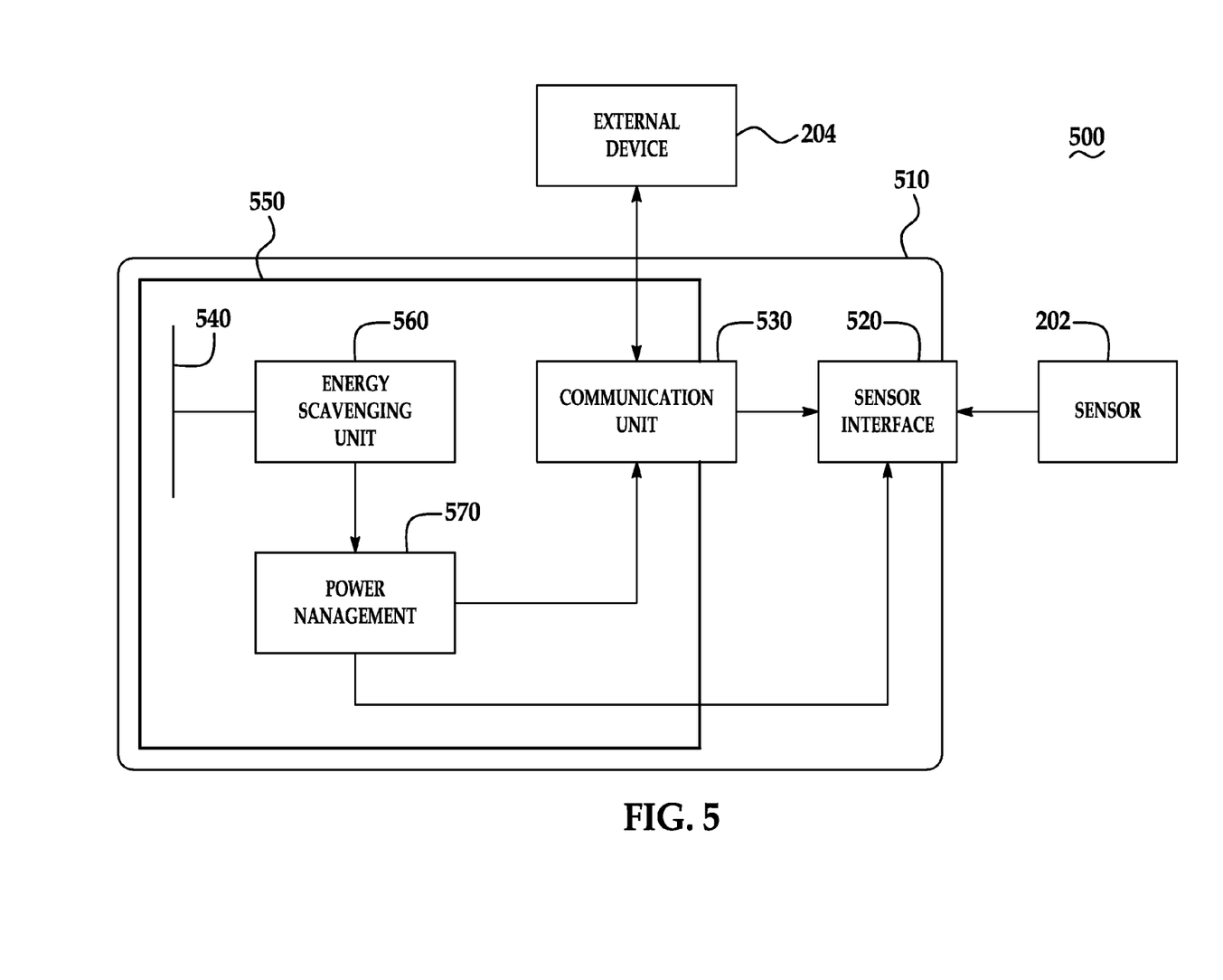
FIG. 5 shows a block diagram of a wirelessly powered health monitor device in accordance with embodiments of this disclosure.

FIG. 5 shows a block diagram of a wirelessly powered health monitor device 500 in accordance with embodiments of this disclosure. The wirelessly powered health monitor device 500 may be used for determining a concentration of an analyte in blood or interstitial fluid and may communicate in a wireless communication system, such as the wireless system shown in FIG. 1, using power harvested from wireless communication signals. For example, the wirelessly powered health monitor device 500 may receive fluid samples, or sample data, from a sensor unit 502, such as the sensor unit 110 shown in FIG. 1, and may wirelessly transmit data to an external device 504, such as the data processing unit 140 shown in FIG. 1. The wirelessly powered health monitor device 500 may be an electronic device, such as transmitter unit 120 shown in FIG. 1, and may be similar to the health monitor device 200 shown in FIG. 2, except as described herein.

The wirelessly powered health monitor device 500 may include a housing 510, a sensor interface unit 520, a communication unit 530, a wideband wireless communication antenna 540, a magnetic loop wireless communication antenna 550, a power scavenging unit 560, a power management unit 570, or a combination thereof. Although not shown in FIG. 5, the a wirelessly powered health monitor device 500 may include other elements of a health monitor device, which may include a processor, such as the processor 220 shown in FIG. 2, a user interface, such as the user interface 240 shown in FIG. 2, a clock, such as the clock 250 shown in FIG. 2, a data storage unit, such as the data storage unit 260 shown in FIG. 2, or any combination thereof. In some implementations, the wirelessly powered health monitor device 500 may be batteryless.

The wirelessly powered health monitor device 500 may determine a concentration of an analyte in blood or interstitial fluid. For example, the wirelessly powered health monitor device 500 may be an analyte test meter, such as a glucose test meter that may be used for determining an analyte concentration, such as a blood glucose concentration, of a sample for determination of a blood glucose level of a patient, such as a patient with Type-1 or Type-2 diabetes. In some embodiments, the wirelessly powered health monitor device 500 may be a blood glucose meter, a continuous monitor, an insulin pump, a blood pressure meter, a heart rate monitor, a thermometer, or any other health monitor device capable of measuring, monitoring, or storing raw or analyzed medical data electronically.

The housing 510 may physically enclose one or more of the sensor interface unit 520, the communication unit 530, the wideband wireless communication antenna 540, the magnetic loop wireless communication antenna 550, the power scavenging unit 560, or the power management unit 570, and may be configured to fit into a small profile. Although the housing 510 is shown a single physical unit, the housing 510 may be implemented as one or more physical units that may be physically or electronically connected. Although not shown in FIG. 5, the housing 510 may include one or more ports, such as a test strip port, a power port, an audio connection port, or a data connection port. For example, the housing 510 may include a test strip port configured to receive a test strip, which may include a fluid sample, and may be connected to the sensor interface unit 520.

The sensor interface unit 520 may be configured to receive analyte information from the sensor unit 502. For example, the sensor interface unit 520 may be configured to receive a glucose current signal, convert the glucose current signal to a voltage signal, and amplify the voltage signal for use in analog to digital signal conversion. In some embodiments, the sensor interface unit 520 may receive a fluid sample. For example, the sensor unit 502 may be a test strip, and the test strip may transport a fluid sample to the sensor interface unit 520. The sensor interface unit 520 may be configured to analyze the fluid sample to determine an associated analyte level. In some embodiments, the sensor interface unit 520 may receive raw or analyzed data indicating an analyte level associated with a fluid sample analyzed at an external measurement device, such as a continuous analyte monitoring device, via a wireless communication medium, such as radio frequency identification (RFID). For example, the continuous analyte monitoring device may include a transcutaneously implanted sensor, such as an implantable glucose sensor, that may continually or substantially continually measure an analyte concentration of a bodily fluid. In some embodiments, the sensor interface unit 520 may receive analyte related data from the external measurement device periodically, based on a transmission schedule, or may request the data from the external measurement device.

Although not shown separately, the health monitor device may include a processor, such as the processor 220 shown in FIG. 2. The processor may be operatively coupled to sensor interface unit 520, the communication unit 530, the power management unit 570, the power scavenging unit 560, the wideband wireless communication antenna 540, or the magnetic loop wireless communication antenna 550. The processor may be configured to receive signals, such as amplified analog voltage signals, from the sensor interface 520, and to convert the analog signals into digital signals, using, for example, analog to digital signal conversion circuitry. The processor may be configured to send the digital signals to the communication unit 530 for transmission to the external device 504.

The communication unit 530 may communicate with an external device 504, such as the receiver unit 130 shown in FIG. 1. For example, the communication unit 530 may be configured to communicate with a smartphone via a wireless communication link. In some embodiments, the communication unit 530 may be configured to transmit analyte information to the external device. In some implementations, the communication unit 530 may be an RF transmitter, such as the RF transmitter 206 shown in FIG. 2, and may communicate using a wireless communication protocol, such as an 802.11 protocol, a Bluetooth® RF protocol, a cellular protocol, or any other wireless protocol. In some embodiments, the communication unit 530 may include a receiver, a transmitter, or a transceiver.

In some embodiments, the communication unit 530 may communicate using a short-range low-energy wireless communication protocol, such as NFC or RFID. Communicating using a low-energy wireless communication protocol may allow the communication unit 530 to use substantially less power than communicating using other wireless communication protocols. For example, using a low-energy wireless communication protocol, the communication unit 530 may have a lower duty cycle and may actively operate less frequently, for shorter periods of time, or both.

In some embodiments, the health monitor device 500 may communicate with the external device 504 indirectly via another device, or series of devices. For example, the health monitor device 500 may communicate with the external device 504 via a network, wherein the health monitor device 500 may transmit signals to, for example, an access point (not shown), and the access point may transmit the signals to the external device 504, in the same or a different format, via one or more other devices in a network.

The wideband wireless communication antenna 540 may be configured to receive energy from a wireless signal, such as high frequency electromagnetic field energy emitted by the external device 504. For example, the external device 504 may be cellular telephone and the wideband wireless communication antenna 540 may receive electromagnetic field energy from cellular telephone communication performed by the external device 504. The wideband wireless communication antenna 540 may receive energy inductively, capacitively, or radiatively.

The magnetic loop wireless communication antenna 550, may be configured to receive energy from a near field wireless signal, such as magnetic field energy generated by a short-range low-energy communication unit in the external device 504, such as an NFC communication unit or an RFID communication unit. The magnetic loop wireless communication antenna 550 may receive energy inductively, capacitively, or radiatively.

The power scavenging unit 560 may include circuitry, such as a rectifier circuit, and may harvest electromagnetic field energy from the wideband wireless communication antenna 540, the magnetic loop wireless communication antenna 550, or both. In some implementations, the power scavenging unit 560 may be operatively coupled with other elements of the health monitor device 500 to provide power to those elements.

The power management unit 570 may be operatively coupled to elements of the health monitor device 500, such as the sensor interface 520, and may manage the distribution of power from the power scavenging unit 560 to the elements of the health monitor device 500. Managing the distribution of power may include filtering and regulating the power.

In some embodiments, the power management unit 570 may include a power reservoir, which may receive and store power from the power scavenging unit 560. For example, when the health monitor device 500 is not in an active mode, received power may be stored in the power reservoir, and when the health monitor device 500 is in an active mode, power stored in the power reservoir may distributed to the health monitor device 500.

Although shown as separate elements, the sensor interface unit 520, the communication unit 530, the wideband wireless communication antenna 540, the magnetic loop wireless communication antenna 550, the power scavenging unit 560, or the power management unit 570, or any combination thereof, may be integrated in one or more electronic units, circuits, or chips.

Although not explicitly shown in FIG. 5, the wirelessly powered health monitor device 500 may be implemented as a solid flat molded unit without mechanical elements. Mass production of the wirelessly powered health monitor device 500 may be relatively inexpensive.

Figure 6:
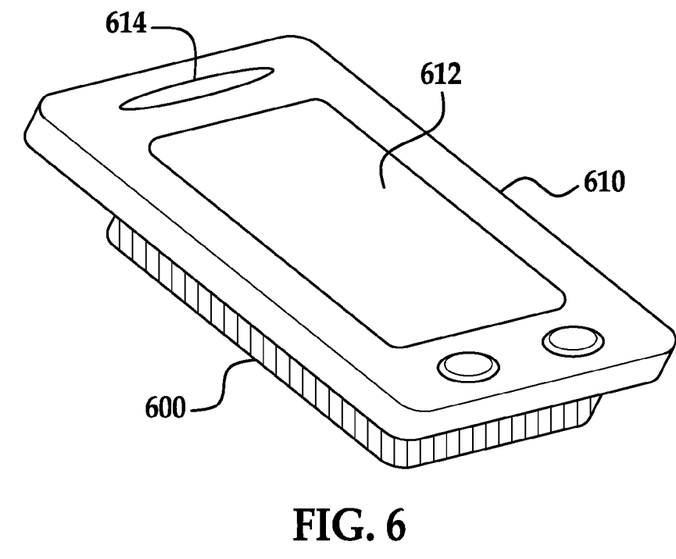
FIG. 6 shows a perspective view diagram of a wirelessly powered health monitor device and external device in accordance with embodiments of this disclosure.

FIG. 6 shows a perspective view diagram of a health monitor device 600, such as the wirelessly powered health monitor device 500 shown in FIG. 5, positioned in close proximity, or attached, to an external device 610, such as the receiver 130 shown in FIG. 1, for short-range, low-energy wireless communication of analyte data in accordance with embodiments of this disclosure.

In some implementations, the health monitor device 600 may be configured with a small physical footprint, such as in a solid, flat shape as shown. For example, the health monitor device 600 may be configured as a case for a glucose meter or a cell phone.

In some implementations, the external device 610 may include a user interface for presenting the analyte data. The external device 610 may control the wirelessly powered health monitor device 600. For example, the external device 610 may receive user input and may control the wirelessly powered health monitor device 600 to perform tests or communicate analyte information. The external device 610 may include a graphical display unit 612, which may be configured to display a visual representation of the analyte data, and an audio presentation unit 614, which may be configured to present an audible representation of the analyte data.

Figure 7:
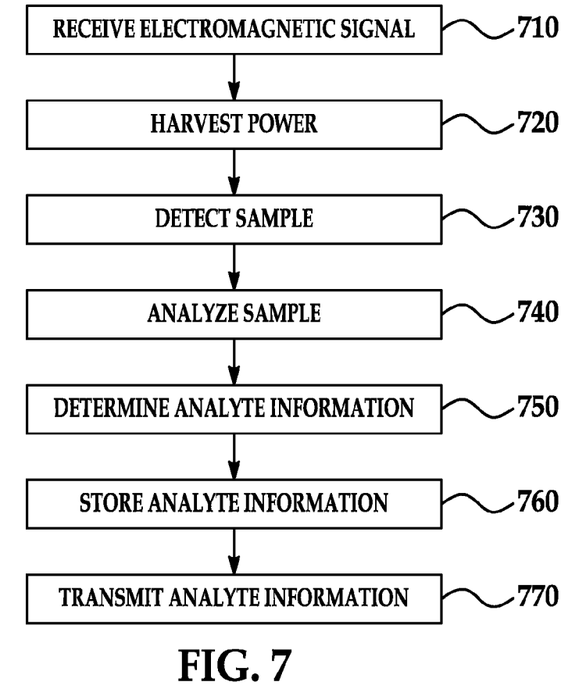
FIG. 7 shows an example of wirelessly powered wireless communication of analyte data in accordance with embodiments of this disclosure.

FIG. 7 shows an example of wirelessly powered wireless communication of analyte data in accordance with embodiments of this disclosure. In some embodiments, a wirelessly powered health monitor device, such as the wirelessly powered health monitor device 500 shown in FIG. 5, may perform wirelessly powered wireless communication of analyte data with an external device which may include transmitting health monitoring information, such as analyte information, to the external device. Wirelessly powered wireless communication of analyte data of may include receiving an electromagnetic signal at 710, scavenging power at 720, detecting a sample at 730, analyzing the sample at 740, determining an analyte concentration at 750, storing analyte information at 760, transmitting an indication of the analyte concentration at 770, or a combination thereof.

An electromagnetic signal may be received at 710. For example, the wirelessly powered health monitor device may receive a short-range low-energy electromagnetic signal, such as an RFID signal or a NFC signal, or the wirelessly powered health monitor device may receive a wideband electromagnetic signal, such as a cellular telephone signal (EDGE, UMTS, HSPA, LTE, or the like) or a wireless networking signal (802.11, or the like). In some embodiments, the wirelessly powered health monitor device may receive a wideband electromagnetic signal and a short-range low-energy electromagnetic signal.

Power may be harvested (scavenged) from the received electromagnetic signal at 720. The receive power may be distributed to elements of the wirelessly powered health monitor device to power the respective elements. In some embodiments, power may be harvested while the wirelessly powered health monitor device is in an inactive mode, may be stored in a power reservoir, and stored power may be used to power, or partially power, the wirelessly powered health monitor device in an active mode.

A sample, such as a blood sample, may be identified at 730. For example, the health monitor device may include a sensor interface, such as the sensor interface unit 560 shown in FIG. 5, which may be configured to receive a fluid sample, such as a fluid sample transported via a test strip. In some embodiments, the sample may be identified by an external measurement device, such as a continuous analyte monitoring device, configured to communicate with the health monitor device using, for example, a short range wireless communication method, such as RFID or NFC. For example, the continuous analyte monitoring device may include a transcutaneously implanted sensor that may continually or substantially continually measure an analyte concentration of a bodily fluid.

The sample may be analyzed to determine a corresponding analyte level, such as a glucose level, at 740. For example, the health monitor device may include a processor, such as the processor 220 shown in FIG. 2, configured to analyze the sample. In some embodiments, the sample may be analyzed by an external analysis device, such as a continuous analyte monitoring device, configured to communicate with the health monitor device.

An analyte concentration may be identified at 750. For example, the analyte concentration may be identified based on the sample analysis at 740. In some embodiments, the analyte concentration may be received from an external analysis device, such as a continuous analyte monitoring device, configured to communicate with the health monitor device. In some embodiments, the analyte concentration may be identified based on stored information, such as previously stored raw or analyzed sample data.

In some embodiments, raw or analyzed analyte information, such the analyte concentration identified at 750, may be stored at 760. For example, health monitor device may include a data storage unit, such as the memory 260 shown in FIG. 2, a processor, such as the processor 220 shown in FIG. 2, a sensor interface, such as the sensor interface unit 520 shown in FIG. 5, or a combination thereof, and the processor, the sensor interface, or a combination thereof, may identify the analyte concentration based on raw or analyzed analyte data stored on the data storage unit.

An indication of the analyte concentration may be transmitted to the external device at 770. For example, the indication of the analyte concentration may be transmitted from the health monitor device to the external device using, for example, a short-range low-energy wireless communication link, such as an NFC communication link. In some embodiments, transmitting the indication of the analyte concentration may include transmitting raw or analyzed analyte information. In some embodiments, transmitting the indication of the analyte concentration may include transmitting health care instructions. In some embodiments, transmitting the indication of the analyte concentration may include synchronizing information between the health monitor device and the external device.

Figure 8:
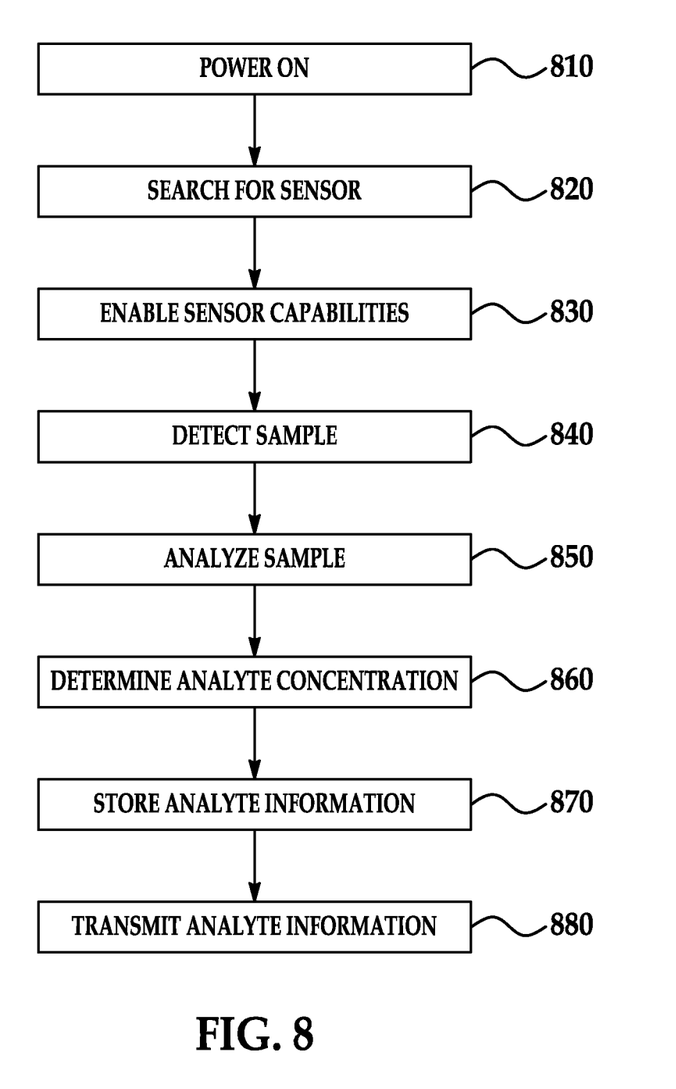
FIG. 8 is an example of enabling suppressed capabilities in accordance with embodiments of this disclosure.

FIG. 8 an example of enabling suppressed capabilities in accordance with embodiments of this disclosure. In some implementations, a health monitor device may include a first set of capabilities (monitor capabilities) associated with monitoring and analysis of analyte data receive via a fluid at the health monitor device, such as a fluid receive via a test strip, and a second set of capabilities (sensor capabilities) configured for monitoring and analysis of analyte data receive from an external sensor, such as a continuous analyte monitoring device.

Prior to activation, the monitor capabilities may be active or enabled, such that the monitor capabilities may be functional and available via the health monitor device, and the sensor capabilities may be inactive, suppressed, hidden, or disabled, such that the sensor capabilities may be non-functional and may be unavailable via the health monitor device.

Suppressing the sensor capabilities may include disabling, or not enabling, capabilities of the health monitor device. For example, a sensor interface for communicating with a sensor device may be disabled. Similarly, user interface features of the health monitor device associated with the sensor interface may be disabled or hidden. In some embodiments, the user interface capabilities associated with the sensor may be provided by an external device and may be hidden on the external device.

In some implementations, a health monitor device, such as the health monitor device 200 shown in FIG. 2 or the health monitor device 500 shown in FIG. 5, may include suppressed capabilities that may be enabled in response to detecting an enabling device, such as a sensor. Enabling suppressed capabilities may include powering on at 810, searching for a sensor at 820, enabling suppressed capabilities at 830, detecting a sample at 840, analyzing the sample at 850, determining an analyte concentration at 860, storing analyte information at 870, transmitting analyte information at 880, or a combination thereof.

The health monitor device may be powered on at 810. Powering on may include enabling a sensor interface for a defined period of time. For example, the sensor interface may include circuitry for communicating with an external sensor, such as a continuous analyte monitoring device, and the communication circuitry may be enabled. In some embodiments, the sensor interface may be temporarily enabled in response to user input, such as a manual activation feature.

The health monitor device may search for a sensor at 820. Searching for the sensor may include transmitting a signal, such as a beacon signal, for a determined period of time, such as 15 seconds. If a sensor is not detected, the health monitor device may terminate transmitting the signal and may disable the temporarily enabled sensor interface. In some embodiments, the health monitor device may search for a sensor in response to user input.

If a sensor is detected, the health monitor device may enable the sensor capabilities at 830. In some embodiments, enabling the sensor capabilities may include enabling a sensor interface configured to receive raw or analyzed analyte information from an external device, such as a continuous analyte monitoring device, configured to communicate with the health monitor device using, for example, a short range wireless communication method, such as RFID or NFC. In some embodiments, enabling the sensor capabilities may include enabling user interface capabilities of the health monitor device. In some implementations, enabling the sensor capabilities may include enabling sensor capabilities on an external device. For example, enabling the sensor capabilities may include activating a sensor, enabling user interface capabilities on an external device, or both. In some embodiments, enabling the sensor capabilities may include enabling product labeling, such as product labeling stored on the health monitor device.

In some implementations, an unlocking device, such as a non-functional sensor or a ROM calibrator, may be detected at 820 and the sensor capabilities may be enabled. In some implementations, the sensor capabilities may be enabled in response to user input. For example, the health monitor device may receive user input indicating an enabling instruction, such as an unlock code, and the sensor capabilities may be enabled.

A sample, such as a blood sample, may be identified at 840. For example, a sensor may not be detected at 820 and the monitor capabilities may include a sensor interface configured to receive a fluid sample, such as a fluid sample transported via a test strip. In another example, a sensor may be detected at 820 and the sensor capabilities may include a sensor interface configured to receive sample information identified by an external measurement device, such as a continuous analyte monitoring device, configured to communicate with the health monitor device using, for example, a short range wireless communication method, such as RFID or NFC.

The sample may be analyzed to determine a corresponding analyte level, such as a glucose level, at 850. For example, the health monitor device may include a processor, such as the processor 220 shown in FIG. 2, configured to analyze the sample. In some embodiments, a sensor may be detected at 820 and the health monitor device may be configured to receive sample information analyzed by an external analysis device, such as a continuous analyte monitoring device.

An analyte concentration may be identified at 860. For example, the analyte concentration may be identified based on the sample analysis at 850. In some embodiments, a sensor may be detected at 820 and the health monitor device may be configured to receive the analyte concentration from an external analysis device, such as a continuous analyte monitoring device. In some embodiments, the analyte concentration may be identified based on stored information, such as previously stored raw or analyzed sample data.

In some embodiments, raw or analyzed analyte information, such the analyte concentration identified at 860, may be stored at 870. For example, health monitor device may include a data storage unit, such as the memory 260 shown in FIG. 2, a processor, such as the processor 220 shown in FIG. 2, a sensor interface, such as the sensor interface unit 520 shown in FIG. 5, or a combination thereof, and the processor, the sensor interface, or a combination thereof, may identify the analyte concentration based on raw or analyzed analyte data stored on the data storage unit.

An indication of the analyte concentration may be transmitted to the external device at 880. For example, the indication of the analyte concentration may be transmitted from the health monitor device to the external device using, for example, a wireless communication link, such as an NFC communication link, a Bluetooth® communication link, or a wireless LAN communication link. In some embodiments, transmitting the indication of the analyte concentration may include transmitting raw or analyzed analyte information. In some embodiments, transmitting the indication of the analyte concentration may include transmitting health care instructions. In some embodiments, transmitting the indication of the analyte concentration may include synchronizing information between the health monitor device and the external device.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

The invention claimed is:

1. An apparatus, comprising:
    a housing;
    a memory unit having computer executable instructions stored thereon;
    a wireless communication interface;
    and
    a processor configured to execute the computer executable instructions stored in the memory unit, wherein execution of the computer executable instructions causes the processor to:
        cause a search for an external sensor while one or more user interface (UI) capabilities of the apparatus are disabled, the one or more UI capabilities being associated with the external sensor, wherein the search for the external sensor includes wireless transmission of a signal adapted to detect the external sensor, and in response to detection of the external sensor, enable one or more disabled UI capabilities associated with the external sensor and cause display of an analyte concentration associated with a measurement made by the external sensor.

2. The apparatus of claim 1, wherein the wireless communication interface is configured to perform wireless communication according to a Bluetooth or a Bluetooth Low-Energy communication protocol.

3. The apparatus of claim 2, wherein the transmission of the signal occurs according to the Bluetooth or Bluetooth Low-Energy communication protocol.

4. The apparatus of claim 1, wherein the transmission of the signal occurs for a determined period of time.

5. The apparatus of claim 4, wherein execution of the computer executable instructions further causes the processor to terminate the transmission of the signal in response to not detecting the external sensor within the determined period of time.

6. The apparatus of claim 1, wherein the transmission of the signal occurs in response to powering on the apparatus.

7. The apparatus of claim 1, wherein the external sensor includes a portion positioned through a skin surface of a user in fluid contact with a bodily fluid of the user.

8. The apparatus of claim 1, further comprising a monitor adapted to analyze fluid on a test strip.

9. The apparatus of claim 8, wherein capabilities associated with the monitor adapted to analyze fluid on the test strip are enabled while the one or more UI capabilities associated with the external sensor are disabled.

10. A method for enabling one or more user interface (UI) capabilities of an apparatus, wherein the UI capabilities are associated with an external sensor, the method comprising:
searching for the external sensor while the one or more UI capabilities associated with the external sensor are disabled, wherein searching for the external sensor includes transmitting a signal adapted to detect the external sensor; and
in response to detecting the external sensor, enabling one or more disabled UI capabilities associated with the external sensor and causing display of an analyte concentration associated with a measurement made by the external sensor.

11. The method of claim 10, further comprising performing, by a wireless communication interface of the apparatus, wireless communication according to a Bluetooth or a Bluetooth Low-Energy communication protocol.

12. The method of claim 11, wherein transmitting the signal includes using the Bluetooth or Bluetooth Low-Energy communication protocol.

13. The method of claim 10, wherein transmitting the signal occurs for a determined period of time.

14. The method of claim 13, further comprising terminating the transmission of the signal in response to not detecting the external sensor within the determined period of time.

15. The method of claim 10, wherein transmitting the signal occurs in response to powering on the apparatus.

16. The method of claim 10, wherein the external sensor includes a portion positioned through a skin surface of a user in fluid contact with a bodily fluid of the user.

17. The method of claim 10, wherein the apparatus includes a monitor adapted to analyze fluid on a test strip.

18. The method of claim 17, wherein capabilities associated with the monitor adapted to analyze fluid on the test strip are enabled while the one or more UI capabilities associated with the external sensor are disabled.

* * * * *